(12) United States Patent
Colon

(10) Patent No.: US 6,587,203 B2
(45) Date of Patent: Jul. 1, 2003

(54) SORT STREAM STABILIZER FOR FLOW CYTOMETER

(75) Inventor: Christopher Colon, Brooklyn, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 93 days.

(21) Appl. No.: 09/789,119

(22) Filed: Feb. 20, 2001

(65) Prior Publication Data

US 2001/0033380 A1 Oct. 25, 2001

Related U.S. Application Data

(60) Provisional application No. 60/188,475, filed on Mar. 10, 2000, and provisional application No. 60/183,250, filed on Feb. 17, 2000.

(51) Int. Cl.[7] .............................................. G01N 21/06
(52) U.S. Cl. ...................... 356/436; 356/440; 356/436; 356/340; 356/39
(58) Field of Search .............................. 356/73, 39, 40, 356/343, 340, 440, 432, 436, 338

(56) References Cited

U.S. PATENT DOCUMENTS

| | | | | |
|---|---|---|---|---|
| 4,906,095 A | * | 3/1990 | Johnston | 356/484 |
| 5,367,474 A | | 11/1994 | Auer et al. | |
| 5,374,398 A | * | 12/1994 | Isami et al. | 137/88 |
| 5,641,457 A | * | 6/1997 | Vardanega et al. | 250/461.2 |
| 5,928,880 A | * | 7/1999 | Wilding et al. | 204/194 |
| 6,077,665 A | * | 6/2000 | Weirich et al. | 435/6 |
| 6,200,101 B1 | * | 3/2001 | North, Jr. | 417/36 |

* cited by examiner

Primary Examiner—Michael G. Lee
Assistant Examiner—Steven S. Paik
(74) Attorney, Agent, or Firm—Quarles & Brady LLP

(57) ABSTRACT

A flow cytometer includes a temperature regulator that maintains the temperature of the piezoelectric actuator sufficiently constant so as to produce a consistent predetermined oscillation frequency, and corresponding consistent predetermined droplet break-off point.

20 Claims, 2 Drawing Sheets

SORT STREAM STABILIZER FOR FLOW CYTOMETER

CROSS-REFERENCE TO RELATED APPLICATIONS

The present application claims priority to provisional application 60/188,475, filed Mar. 10, 2000, and entitled "Sort Stream Stabilizer Device" and further claims priority to provisional application 60/183,250, filed Feb. 17, 2000, and entitled "Sort Stream Stabilizer for Flow Cytometer" the disclosures of which are hereby incorporated by reference as if set forth in their entirety herein.

BACKGROUND OF THE INVENTION

The present invention relates generally to flow cytometers and, in particular, relates to a method and apparatus for producing a consistent droplet break-off point.

Flow cytometers are used to analyze particles, such as blood cells, in a liquid suspension. For example a particular blood cell of interest may be present among various types of blood cells. In order to physically separate cells of interest, the cell suspension is presented within a flow cytometer's flow cell through a sample injection tube where it is hydrodynamically focused within a pressurized sheath stream of electrolyte solution. This action produces a laminar flow of cells which is subjected to illumination at an analysis location, such as by a laser beam. To enhance the distinctive light reflective characteristics of the various cell types, the cells may be treated with fluorescent dyes or markers prior to testing with the flow cytometer. The flow cytometer measures the amount of light scattered in the forward and in the 90 degree angle directions from the laser and from any other emitted light that would result from laser excited fluorochromes which may be present on or in the cell of interest. Additionally, the instrument measures the amount of fluorescent light emitted by each particle as well as the corresponding light scatter patterns. These signals are collected in the form of light energy, and converted to electrical energy, and subsequently digitized and plotted on user-defined histograms.

Flow cytometric cell sorters thus have the ability to separate or identify particles of interest from other unwanted particles. In particular, the cell sorter is equipped with a bimorph crystal and an electric oscillator that vibrate the sample stream, causing it to break into free droplets at a specific user-defined droplet break-off point after having been identified for subsequent separation or sorting. The flow cytometer operator determines the population to be sorted during analysis by setting a user-defined sort region identifying particles that meet specific light-scatter and fluorescence criteria. The instrument is also programmed to apply an electrical charge to the droplet containing those particles of interest at a point downstream of the analysis location. As the now charged droplet, containing the particle of interest, then moves down into the area of the cell sorter's oppositely-charged deflection plates. It is pulled away from the uncharged droplets containing unwanted cells, and pulled towards the oppositely charged deflection plate, and onto a glass microscope slide or into a sample collection tube. The uncharged droplets containing unwanted particles flow into a drain and into a waste collection tank.

One example of such a flow cytometer is described in U.S. Pat. No. 5,367,474, entitled "Flow Cytometer," and assigned to Coulter Corp, Miami, Fla., the disclosure of which is hereby incorporated by reference as if set forth in its entirety herein.

During a routine period of instrument preparedness (usually an 8 hour day for a core facility) the sort stream of conventional cytometers becomes unstable. At the start-up of the sorter instrument, the crystal's oscillation frequency will be established within a reasonable time. Sort purity and recovery are at acceptable levels within the time that the bimorph crystal, also known as a crystal assembly or piezoelectric crystal, is stable and producing a stable sort stream. As used herein, a stable sort stream is one whose droplet break-off point, defined as that location at which sheath and enclosed sample stream first start to produce separate and distinct droplets, is consistent, thereby facilitating a reliable separation of particles of interest. However, after a period of time, this droplet break-off point will change and cannot be recovered, thereby facilitating unreliable results.

Once this occurs, no current method exists for returning the sort stream's stability to an operational state short of continually changing the bimorph crystal's rate of oscillation. Doing so, however, requires a video camera with high resolution to examine minute changes in the droplet break-off point that are sufficiently miniscule so as to not adversely affect the reliability of the separation, while providing an indication that the oscillation frequency is fluctuating. Software logic is also necessary to vary the supply current to the crystal, along with a monitor is to examine the location of the droplet break-off point. This is undesirable in that the resources required are expensive, and is reactive to changes in oscillation frequency rather than being proactive.

What is therefore needed is a stable cytometer that proactively produces a consistent droplet break-off point to enable the reliable determination of a particle of interest.

SUMMARY OF THE INVENTION

The present invention recognizes that significant temperature fluctuations in the ambient environment surrounding the piezoelectric crystal occur due to significant changes in ambient room temperature and instrument temperature changes caused by heat-producing components within the instrument. This results in corresponding temperature fluctuations of the crystal itself. When these temperature fluctuations are too large, the crystal and the sort stream become unstable and the results unreliable. Depending on the quality of the crystal, temperature fluctuations as little as 1° C. may affect the reliability. Accordingly, the preferred embodiment of the present invention comprises a cytometer that maintains the temperature of the piezoelectric crystal within a suitable range so as to maintain the stability of the resultant sort stream produced by the cytometer, thereby ensuring accurate results.

In accordance with one aspect of the invention, a flow cytometer includes a flow cell body having an inlet end for receiving sample particles, and an outlet end for delivering a stream of the sample particles to a analysis location, a laser mechanism directing a laser beam towards the sample particles at the analysis location, a sensor operable to measure the optical characteristics of the sample particles to identify select ones of the particles of interest, an actuator in mechanical communication with the flow cell body and oscillating at a frequency sufficient so as to separate the particles at a predetermined separation location, a temperature regulator in thermal communication with the actuator and operable to maintain the actuator within a predetermined temperature range.

This and other aspects of the invention are not intended to define the scope of the invention for which purpose claims are provided. In the following description, reference is made to the accompanying drawings, which form a part hereof, and in which there is shown by way of illustration, and not limitation, a preferred embodiment of the invention. Such embodiment also does not define the scope of the invention and reference must be made therefore to the claims for this purpose.

DESCRIPTION OF THE PREFERRED EMBODIMENT

Figure 1:
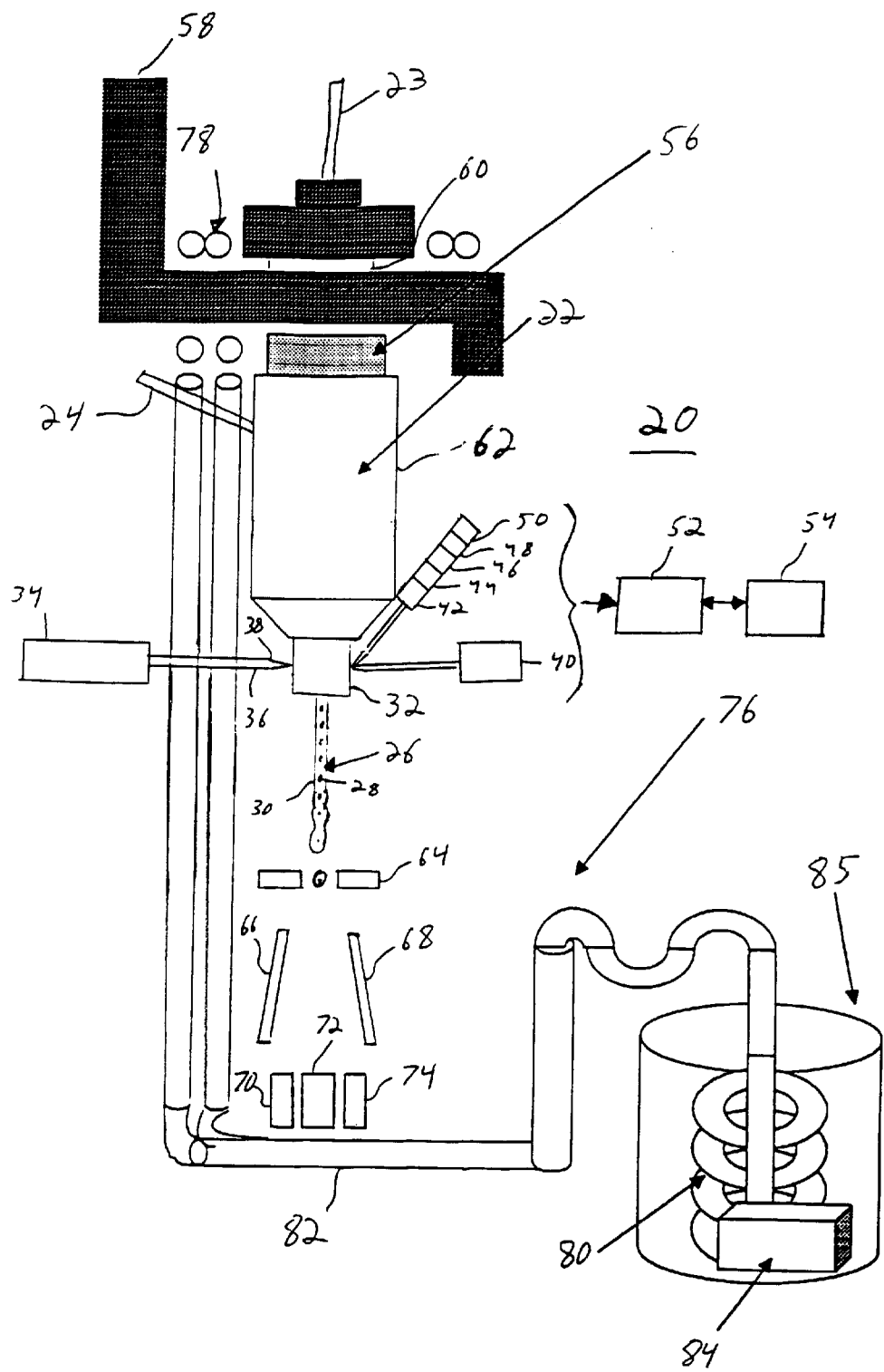
FIG. 1 is a schematic side elevation view a flow cytometer's flow cell area having a temperature regulator constructed in accordance with a preferred embodiment of the invention.
Figure 2:
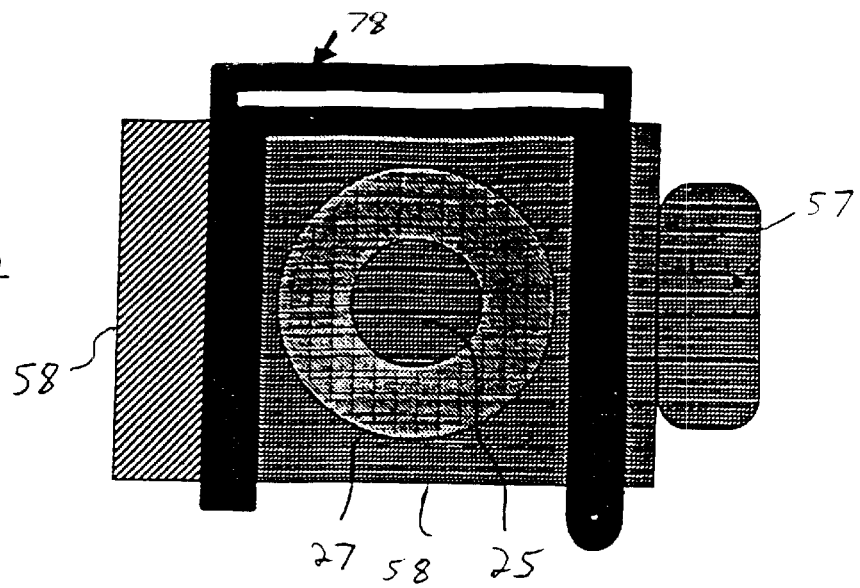
FIG. 2 is a top plan view of the flow cytometer's flow cell area illustrated in FIG. 1.

Referring initially to FIGS. 1 and 2, the flow cell area of a flow cytometer 20 includes a flow cell 22 body having a sample inlet 23 for receiving a sample containing particles 26 such as human blood cells, and a sheath inlet 24 for receiving a sheath fluid 30, such as a saline solution. The inlet 23 is connected to an inner knurled knob 25, which is further fastened to the flow cell body 22 via an outer knurled knob 27. The cell or particle suspension joins with the sheath fluid 30 to produce a mixture 26 which, more accurately, is a combined unit of sample solution which has been hydrodynamically, centrally focused such that the particle is driven to the center of the sheath fluid. The sheath fluid 30 allows a cell of interest to be electrostatically charged, as will be described in more detail below. Flow cell assembly 22 includes an analysis location 32 at its lower end, through which the mixture 26 flows. A laser beam module 34 is positioned at the analysis location and emits a laser beam 36 perpendicular to the path of the stream. The beam 36 is directed through focusing optics 38 and into the analysis location 32, where it is refracted by the cells 28.

The emitted forward angle light is measured via a first photo-detector 40, and the emitted 90 degree angle light is measured by a second photo-detector 42. In particular, photo-detector 40 is positioned on the opposite side of analysis location 32 with respect to laser module 34, and in alignment with the laser beam 36, such that detector 40 measures the light that has been refracted in the forward direction. The photo-detector 42 is placed perpendicular to the laser beam path to measure light scattered toward detector 42, which is also known as side scatter. FIG. 1 illustrates the side scatter detector 42, though not in the perpendicular position, for illustration purposes only, it being appreciated that, in operation, detector 42 is positioned perpendicular to laser beam 26 as described herein.

It should be appreciated that the cells or particles may be pre-treated with fluorescent dyes, in which case additional photomultiplier tubes (PMT's) 44–50 are positioned perpendicular to the laser beam 36 to measure the fluorescent emission from these particles. The fluorescent emission is caused by the excitation of the staining material on the cells or particles 28 by the laser beam 36.

The light sensors 40 and 42 are used to collect information regarding the size, granularity and uptake of the fluorescent markers of the cell being detected, which is used to identify the particular type of cell. Accordingly, electronic pulses emanate from light sensors 40 and 42–50 and are sent to processor 52, which digitizes the electronic pulses 52 and is further coupled to an I/O device 54, which may comprise a conventional pc, keyboard, and monitor. The I/O device 54 is used to set user preferences regarding the type of cell to be analyzed, sort criteria used to separate the particles, the type of stain that is placed on the cells 28, and the like. I/O device 54 sends the user preference data to processor 52, which, based also on data collected from sensors 40 and 42–50, identifies the cells of interest. Processor 52 then forwards information regarding the cell of interest to the I/O device 54, which may display this information to the user in one of several user-defined formats.

An electromechanical actuator 56, which comprises a piezoelectric crystal in accordance with the preferred embodiment, is attached at its outer edges to the peripheral edges of a bore that extends through a metallic flow cell assembly clamp 58. Upper and lower portions 60 and 62, respectively, of the flow cell 22 are threaddedly connected so as to partially encase the crystal therein. Crystal 56 receives power via an electrical plug 57. Accordingly, vibration of the crystal 56 at a predetermined frequency correspondingly vibrates the flow cell body 22. This agitates the blood cell/sheath fluid mixture 26 to facilitate the separation of the blood cells 28 at a position downstream of the laser beam 36 for individual analysis, and retention of only those cells whose optical characteristics are in accordance with the cells identified as being of interest.

In operation, once the focused particles or cells 26 flow into the analysis location 32, they are exposed to the laser beam 36, and their light characteristics are measured. Processor 52 analyzes the measured light characteristics of the cells, and determines whether a cell of interest has been identified based on the user preferences entered via I/O device 54. After the focused particles or cells 26 have been exposed to laser beam 36, the oscillation frequency of the piezoelectric crystal 56 is such that the stream 26 begins to undulate immediately downstream of the laser 34, and breaks up before flowing into area of a charging collar 64. Accordingly, each individual cell 28 is exposed to the charging collar 64, where each cell of interest is given either an electrostatic charge by the collar 64. The ionic sheath fluid 30 surrounding the blood cell 28 allows the particle to become charged by the collar 64. The particle then travels between a first, positively charged, deflection plate 66 and a second, negatively charged, deflection plate 68.

First, second, and third receptacles 70, 72, and 74, respectively, are disposed downstream of the deflection plates 66 and 68. In particular, first receptacle 70 is disposed in general alignment with the first deflection plate 66, and third receptacle 74 is disposed in general alignment with the second charged plate 68. Second receptacle 72 is centrally disposed between the first and third receptacles 70 and 74, and is substantially equidistant from first and second plates 66 and 68. When the stream passes through the laser module 34, it is in initial alignment with the second receptacle 72, which serves as a waste receptacle as will be become apparent from the description below.

As described above, when a cell is examined and determined to be of interest, the droplet containing that cell will be given an electrostatic charge by the charging collar 64. As that droplet continues past the collar 64 and towards the deflection plates 66 and 68, it will be drawn towards that plate that is charged opposite with respect to the charge administered by the charging collar. If the charged droplet needs to be directed toward the other direction, the polarity of the plates 66 and 68 may be reversed such that the droplet is attracted toward the opposite plate and corresponding receptacle. The droplet will not be pulled into contact with deflection plates 66 or 68. Rather, the charge administered by collar 64 is only strong enough such that the droplet and its contained cell is drawn into alignment with the receptacle 70 or 74 for storage and subsequent examination. The deflection plates 66 and 68 are angled outwardly with respect to the stream 26 so as to further prevent the cell of interest from contacting either plate. If a cell is determined not to be of interest, it will not be charged by the collar 64, and will continue unimpeded downstream and ultimately into the second receptacle 72, where it may be subsequently discarded.

It has been observed that the operating oscillation frequency of piezoelectric crystals may fluctuate when the temperature of the crystal experiences fluctuations exceeding as little as approximately 1° C. For example, modest changes in room temperature throughout a given day coupled with heat emitted by the components of the cytometer, such as laser module 34, can raise or lower the temperature of the crystal significantly. The corresponding change in crystal frequency results in an unpredictable change in the droplet break-off point of the mixture 26. Accordingly, the preferred embodiment of the invention provides an apparatus that maintains the temperature of crystal 56 within a predetermined temperature range that maintains the reliable operation of the crystal. Preferably, the temperature range of the crystal does not exceed approximately 1° C.

One method that could be used to maintain the temperature range of the crystal 56 would be to supply constant heat to the crystal that yields a sufficiently high crystal temperature that renders the crystal substantially impervious to modest fluctuations in ambient temperature. This, however, is impractical as live cells would not be able to survive at these elevated temperatures.

Another method of compensating for frequency fluctuation is to constantly vary the voltage that is applied to the crystal in an attempt to maintain a constant oscillation frequency, which would correspondingly produce the desired droplet break-off point. This method, however, may only be used once the frequency of the crystal has begun producing undesirable results.

Referring still to FIG. 1, the cytometer 20 comprises a temperature regulator 76 configured to maintain the crystal 56 at substantially the same temperature during operation of the cytometer 20. It should be appreciated that "substantially the same temperature" as used herein means that the crystal 56 will not experience temperature fluctuations that are great enough to adversely affect the crystal's oscillation frequency. Furthermore, cells 28 may survive in the temperature achieved in accordance with the preferred embodiment. In particular, the temperature regulator 76 comprises a cooling system including first and second separate heat exchange coils 78 and 80, respectively, made of a heat conducting metal such as copper or aluminum and that are connected to each other by silicone tubing 82. Tubing 82 will not cause any significant gain in temperature of the coolant, which may comprise water, anti-freeze, or a mixture of the two, passing through it.

The first heat exchange coils 78 are connected to the crystal's metallic clamp 58 and, accordingly, to the crystal 56 and absorbs heat such that temperature fluctuations in the ambient environment do not affect the temperature of the crystal. Alternatively, the first coils 78 could be coupled directly to any other component of cytometer 20 that is in suitable thermal communication with crystal 56. The first heat exchange coils 78 may be custom fitted by bending the metal tubing around the clamp 58 and/or flow cell body 22 such that there is sufficient contact with the parts to be cooled. The second heat exchange coils 80 are submerged in a tank 85 which contains a bath of ice and water. The ice bath provides a stable temperature environment which is not affected by modest room temperature fluctuations. Coolant is pumped through the coils at a constant rate under the control of an external electronically operated re-circulation pump 84.

The temperature regulator 76 should be activated prior to starting the cytometer 20, or shortly thereafter, or it may be turned on and kept on for the period of time once stability of the oscillation frequency is established. As a result, the temperature of the crystal 56 is maintained at the temperature of the ice bath, approximately 0° C., which is sufficiently cold to render the crystal effectively impervious to temperature fluctuations in the ambient environment. An ice bath is desirable because its temperature will not fluctuate more than 1° C. once equilibrium of the bath has been established. Because the temperature of the crystal 56 is maintained substantially constant, a consistent crystal vibration frequency is produced which, in turn, results in a reliable droplet break-off point.

Figure 3:
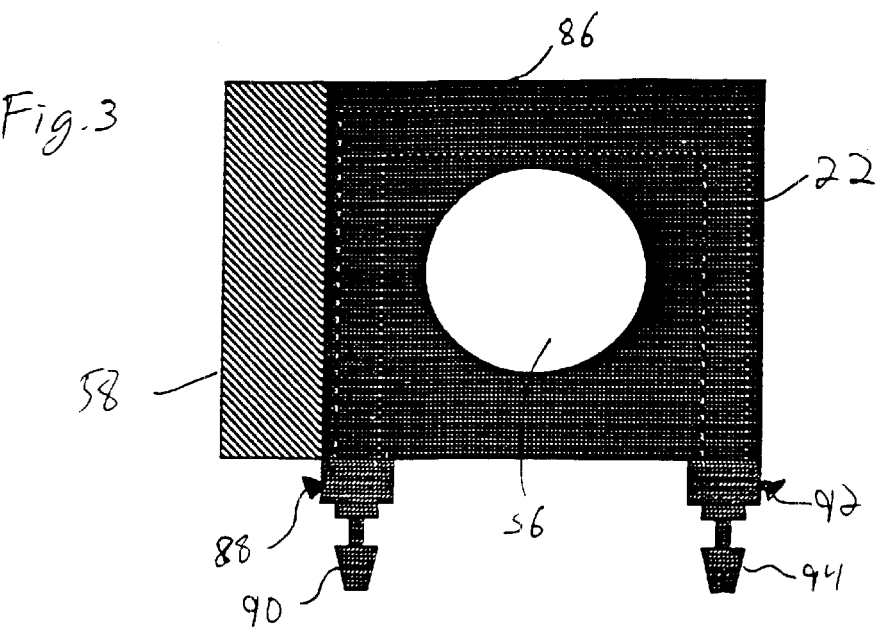
FIG. 3 is a schematic top plan view of the flow cytometer's flow cell area having a temperature regulator constructed in accordance with an alternate embodiment of the invention.

Referring to FIG. 3, a flow cytometer constructed in accordance with an alternate embodiment includes an inner channel 86 disposed within the clamp 58. In particular, the channel extends around the periphery of crystal 56. The channel 86 includes a first inlet end 88 having a corresponding barbed fitting 90 that is received by tubing 82. The channel 88 further includes a terminal outlet end 92 having a corresponding barbed fitting 94 that is received by tubing 82. The tubing has first and second terminal ends (not shown) that are disposed in tank 85. Accordingly, coolant is pumped through the tubing 82, inlet 88, and outlet 92 at a constant rate under the control of pump 84. The coolant is thereby placed in sufficient thermal communication with the crystal so as to prevent fluctuations in temperature of the crystal 56 of such significance that would produce change in the crystal frequency that would correspondingly affect the droplet break-off point, as described above.

Figure 4:
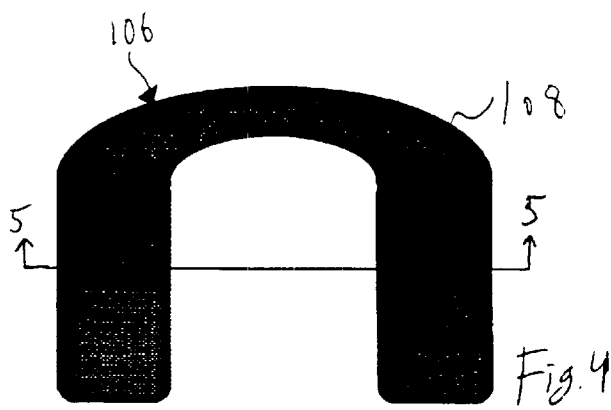
FIG. 4 is a top plan view of a refrigerated pouch operable to cool the piezoelectric crystal of a cytometer in accordance with an alternate embodiment of the invention.
Figure 5:
FIG. 5 is a side elevation view of the refrigerated pouch illustrated in FIG. 4 taken along line 5—5.

Referring now to FIGS. 4 and 5, a temperature regulator constructed in accordance with an alternate embodiment includes a cooling device 106. In particular, the device 106 may comprise a U-shaped molded vinyl sealed container 108 having an interior cavity which is filled with a chilled coolant having a temperature of approximately 0° C. The container 108 is preferably malleable and appropriately sized so as to be fitted around the crystal 56, clamp 58, or flow cell body 22. The container 108 may comprise a frozen cold pack that is replaced as needed to prevent the temperature of crystal 56 from fluctuating. Accordingly, device 106 is placed in thermal communication with crystal 56 such that the parts are cooled sufficiently so as to be effectively impervious to temperature fluctuations of the ambient environment. The device 106 may either be rapidly exchanged with a fresh one after a period of time as described above or, alternatively, the fluid disposed therein may be replenished periodically to provide a constant temperature of approximately 0° C.

Several embodiments of a temperature regulator have been illustrated that are sufficient to prevent the temperature of crystal 56 from fluctuating enough to adversely affect the reliability of the oscillation frequency. It should be appreciated that the present invention includes any temperature regulator that is sufficient to prevent such temperature fluctuations. For example, a fan or other cooling unit (not shown) could be fitted around the crystal 56, flow cell body 22, or clamp 58 such that a cooling environment is produced by sufficient air contact/exchange and fanning of the parts to create a stable, constant low crystal temperature.

The above has been described as a preferred embodiment of the present invention. It will occur to those that practice the art that many modifications may be made without departing from the spirit and scope of the invention. For example, while the coolant has been described as having a temperature of approximately 0° C., it may be held at any temperature sufficient to maintain the temperature of crystal 56 within a suitable range. A temperature of approximately 0° C. is described in accordance with the preferred embodiment due to the fact that this is the temperature range in a ice and water bath which is at equilibrium, and is a relatively easy system to maintain and very stable. Additionally, the scope of the invention is intended to encompass alternative cooling systems, such as a refrigeration system. Accordingly, in order to apprise the public of the various embodiments that may fall within the scope of the invention, the following claims are made.

I claim:

1. A flow cytometer, comprising:
    a flow cell body having an inlet end for receiving sample particles, an outlet end for delivering a stream of the sample particles to an analysis location;
    a laser mechanism directing a laser beam towards the sample particles at the analysis location;
    a sensor operable to measure the optical characteristics of the sample particles to identify select ones of the particles of interest;
    an actuator oscillating the flow cell body at a frequency sufficient so as to separate the particles at a predetermined separation location; and
    a temperature regulator in thermal communication with the actuator and operable to maintain the actuator within a predetermined temperature range.

2. The cytometer as recited in claim 1, wherein the actuator comprises a piezoelectric crystal whose oscillation frequency varies when the actuator temperature falls outside of the predetermined temperature range.

3. The cytometer as recited in claim 1, wherein the oscillation frequency is such that the predetermined separation location is disposed downstream of the analysis location.

4. The cytometer as recited in claim 1, wherein the temperature regulator comprises a cooling system.

5. The cytometer as recited in claim 4, wherein the cooling system comprises:
    a cooling apparatus having a first coil disposed therein, wherein the first coil is maintained at a predetermined temperature;
    a second coil in thermal communication with the actuator;
    a conduit extending from the first coil to the second coil; and
    a pump operable to circulate coolant through the coils.

6. The cytometer as recited in claim 4, wherein the cooling system comprises a container filled with a chilled coolant that is placed in thermal communication with the actuator.

7. The cytometer as recited in claim 6, further comprising a clamp operable to retain the actuator, wherein the container is malleable so as to be fitted to one of the clamp, flow cell body, and actuator.

8. The cytometer as recited in claim 6, wherein the cooling apparatus contains a combination of water and ice.

9. The cytometer as recited in claim 4, wherein the cooling system further comprises:
    an interior channel in thermal communication with the actuator; and
    a tubing member delivering a coolant from a bath to the interior channel.

10. The cytometer as recited in claim 5, wherein the cooling system maintains the temperature of the first coil substantially at 0° C.

11. The cytometer as recited in claim 1, wherein the particles comprise human blood cells.

12. A method for operating a flow cytometer, comprising:
    introducing a quantity of unknown particles into a flow cell body;
    exposing the quantity of unknown particles to light;
    oscillating the flow cell body with an actuator at a predetermined oscillation frequency;
    examining optical characteristics of each of the quantity of unknown particles to identify select particles of interest;
    in response to the oscillation, separating the quantity of particles into a plurality of individual particles; and
    bringing a fluid having predetermined temperature characteristics in thermal communication with the actuator so as to maintain the actuator within a predetermined temperature range.

13. The method as recited in claim 12, wherein the actuator comprises a piezoelectric crystal whose oscillation frequency varies when the actuator temperature falls outside the predetermined temperature range.

14. The method as recited in claim 12, further comprising separating the quantity of particles into individual particles at a predetermined location downstream of the flow cell body in response to the oscillation frequency.

15. The method as recited in claim 12, wherein the bringing step further comprises circulating a coolant from a first coil having a predetermined temperature to a second coil in thermal communication with the actuator.

16. The method as recited in claim 15, wherein the coolant has a temperature of substantially 0° C.

17. The method as recited in claim 12, further comprising placing a cold pack in thermal communication with the actuator.

18. The method as recited in claim 12, wherein the cytometer comprises an interior channel in thermal communication with the actuator, the method further comprising the step of circulating a fluid having a predetermined temperature through the channel.

19. The method as recited in claim 12, wherein the particles comprise human blood cells.

20. The method as recited in claim 12, wherein the introducing step further comprises mixing the particles with a sheath fluid to produce a hydrodynamically focused mixture.

* * * * *

UNITED STATES PATENT AND TRADEMARK OFFICE
CERTIFICATE OF CORRECTION

PATENT NO. : 6,587,203 B2
DATED : July 1, 2003
INVENTOR(S) : Christopher Colon

It is certified that error appears in the above-identified patent and that said Letters Patent is hereby corrected as shown below:

Column 7,
Line 31, "particles, an" should be -- particles, and an --.

Signed and Sealed this

Seventh Day of October, 2003

JAMES E. ROGAN
*Director of the United States Patent and Trademark Office*